(12) United States Patent
Cheng

(10) Patent No.: US 11,446,916 B2
(45) Date of Patent: Sep. 20, 2022

(54) STRETCH LAMINATE

(71) Applicant: Golden Phoenix Fiberweb, Inc., Taipei (TW)

(72) Inventor: Kenneth Cheng, Taipei (TW)

(73) Assignee: GOLDEN PHOENIX FIBERWEB, INC., Taipei (TW)

( * ) Notice: Subject to any disclaimer, the term of this patent is extended or adjusted under 35 U.S.C. 154(b) by 0 days.

(21) Appl. No.: 16/729,296

(22) Filed: Dec. 27, 2019

(65) Prior Publication Data

US 2022/0161540 A1    May 26, 2022

(51) Int. Cl.
| | | |
|---|---|---|
| *B32B 38/00* | (2006.01) | |
| *B32B 37/00* | (2006.01) | |
| *B32B 37/15* | (2006.01) | |
| *B32B 37/26* | (2006.01) | |
| *B32B 38/10* | (2006.01) | |
| *A61F 13/15* | (2006.01) | |

(52) U.S. Cl.
CPC ...... *B32B 38/0012* (2013.01); *B32B 37/0076* (2013.01); *B32B 37/15* (2013.01); *B32B 37/26* (2013.01); *B32B 38/10* (2013.01); *B32B 38/1875* (2013.01); *A61F 13/15699* (2013.01); *B32B 2038/0028* (2013.01); *B32B 2323/00* (2013.01); *B32B 2555/02* (2013.01)

(58) Field of Classification Search
CPC . A61F 13/15699; B32B 38/10; B32B 37/153; Y10T 156/11
See application file for complete search history.

(56) References Cited

U.S. PATENT DOCUMENTS

| | | |
|---|---|---|
| 6,051,177 A | 4/2000 | Ward |
| 6,746,978 B1 | 6/2004 | Ward |
| 6,984,439 B2 | 1/2006 | Topolkaraev |

(Continued)

FOREIGN PATENT DOCUMENTS

| | | |
|---|---|---|
| WO | 2008067463 | 5/2016 |
| WO | 2016079608 | 5/2016 |

*Primary Examiner* — Carson Gross
(74) *Attorney, Agent, or Firm* — Jordan IP Law, LLC

(57) ABSTRACT

A method to manufacture an elastic laminate is disclosed. Thermoplastic Elastomeric Material (TEM) is selected from a polymer supply and fed into an extruder. The TEM film is extruded by the extruder by passing the TEM polymer through an extrusion die head to form a TEM film layer on a carrier web provided by a carrier supply. The TEM film layer is allowed to solidify on the carrier web, thereby forming a first laminate. The first laminate is stored in a first storage prior to being delivered to a delamination unit, which delaminates the first laminate by separating the TEM layer from the carrier web. The delaminated TEM layer is stretched at least in its Machine Direction (MD) in a stretching station via a plurality of web guide means. The stretched TEM layer is positioned between a first envelope web and optionally a second envelope web prior to being delivered to a bonding unit, which connects them to form a second bonded laminate. The second bonded laminate is unstretched and stored in a second storage for a predetermined time. The stored second bonded laminate is wound under controlled tension to form a roll or spool, thereby forming the elastic laminate.

19 Claims, 4 Drawing Sheets

(56) References Cited

U.S. PATENT DOCUMENTS

| | | |
|---|---|---|
| 7,803,244 B2 | 9/2010 | Siqueira et al. |
| 7,910,658 B2 | 3/2011 | Chang |
| 8,133,339 B2 | 3/2012 | Nordang |
| 8,273,068 B2 | 9/2012 | Chang |
| 8,721,827 B2 | 5/2014 | Chang |
| 9,199,410 B2 * | 12/2015 | Floberg ............. A61F 13/15731 |
| 2002/0119300 A1 | 8/2002 | Enewoldsen |
| 2004/0121683 A1 | 6/2004 | Jordan |
| 2006/0148361 A1 * | 7/2006 | Ng .................... A61F 13/15707 |
| | | 442/394 |

\* cited by examiner

STRETCH LAMINATE

FIELD OF THE INVENTION

The present invention relates to a method for the manufacture of an elastic laminate comprising a stretchable film of a Thermoplastic Elastomeric Material (TEM) between nonwoven webs, which is relaxed under non-stretch conditions at least for a predetermined time before it is wound-up for shipment for further conversion, e.g. in the manufacture of hygiene articles, like diapers.

BACKGROUND OF THE INVENTION

Thermoplastic Elastomeric Material (TEM) is a type of polymer comprising both thermoplastic and elastomeric properties. The TEM polymer exhibits an elastic behavior not quite as good as elastomers like SBS or rubber but at better cost. It may be well stretched to moderate elongations under controlled stress conditions and retracts quickly upon removal of the stress but does not regain original dimensions, thereby maintaining a certain amount of elongation. The polymer possesses certain properties, which render the polymer highly beneficial in various industrial applications such as diaper industry, disposable medical apparel manufacturing, disposable sheets, etc. The polymer exhibits moderate to good elastic behavior, recyclable properties, exceptional thermal characteristics, stability, inexpensiveness, etc.

The TEM polymer is bonded to one or more envelope webs for manufacturing an elastic laminate. The envelope webs are made up of a non-woven material that comprises fibrous structures bonded together by entanglement or chemical or thermal fusion bonding. Non-woven webs may have one or more fiber layers, and are highly flexible. The non-woven webs may have apertures of a certain size and therefore are suitable for use in products requiring breathability, but also absorption capability, flexibility, stretch, elasticity, cushioning, sterility, etc. Typical raw materials for manufacturing the non-woven webs are polyester, or polyolefins like polyethylene or polypropylene. Fabrics made up of non-woven webs have a long durability or have short life depending upon the choice of raw material. The non-woven webs are formed by various processes such as meltblowing, spunbonding, coforming, hydroentangling, air-laid and bonded carded web processes.

The elastic laminate is fabricated by bonding a TEM film between one or more non-woven envelope webs. Bonding of the TEM film and the non-woven envelope webs may be performed by applying heat, air, pressure, chemicals, high frequency vibrations, or any other kind of bonding technique already known in the art. The elastic laminate is stretchable in its Machine Direction (MD). Further, the elastic laminate may also be stretched in a Cross Direction (CD). The Machine Direction (MD) stretch may refer to the stretch applied to the laminate in a direction in which the laminate was produced and the Cross Direction (CD) stretch may refer to stretch applied in a direction perpendicular to the Machine Direction (MD). Typically, the Machine Direction (MD) stretch is achieved by having a roller arrangement comprising a number of rollers. Each successive roller in the number of rollers may rotate at a higher speed than the preceding roller. Maximum amount of stretch is accomplished at last stretch roll before entering a bonding unit.

Stretching the elastic laminate in either direction leads to increase in flexibility and elasticity of the laminate. Due to the properties possessed by the TEM polymers, the elastic laminate may upon release of mechanical stress or strain quickly retract to a certain degree, followed by slower retraction to a remaining "permanent set", corresponding to a certain amount of elongation compared to the original length prior to straining.

U.S. Pat. Nos. 6,051,177 and 6,746,978 to Gregory Ward disclose a process and resulting material to expand a precursor web in cross direction. The precursor web is passed through a plurality of rolls, where each roll has a predetermined rotational velocity. The velocity of the rolls is adjusted in order to have cumulative strain rate for all rolls less than 9.5 in/in/min. Tangential distance between each roll is adjusted to attain cumulative strain rate no greater than 9 in/in/min. Temperature is preset at maximum of 70° F. above the precursor web's plastic point. Settings of velocity, tangential distance and temperature lead to decrease in width of the web and increases in length of the web, thereby attaining cross machine direction elasticity in the web.

U.S. Pat. No. 7,803,244 to Siqueira et al. discloses a method to manufacture an elastic non-woven composite by controlling a number of factors leading to form apertures of a certain size in an elastic film bonded to non-woven web. The aperture size depends upon required texture, softness and other aesthetic properties of the elastic non-woven composite. The factors may be material of the elastic film, bonding pattern, tension, bonding conditions, etc. The aperture size may be 200 to about 5000 micrometers under a controlled stretch ratio range of 2.5-7.0 in machine direction, temperature 130° C. to 200° C. In addition, one roll is subjected to a temperature in a range of 50° C. to 120° C.

U.S. Pat. No. 8,133,339 to Nordang discloses a bonding system that bonds stretched materials by applying pressure. Speed of feeding the stretched materials into the bonding system increases as the materials moves along the bonding system. Variation in speed may lead to equal stretching of the materials to be bonded prior to entering a pressure bonder. The linear pressure applied to the materials may be in range of $0.05*10^6$ N/m to $6*10^6$ N/m.

U.S. Pat. No. 9,199,410 to Floberg et al discloses an elastic laminate manufacturing process that performs a multi-step elastic film stretching in machine direction. The elastic film proceeds through a plurality of stretch rolls prior to bonding. Last stretching step leads to 5 and 25% of the total stretching, thereby stretching the film from 1.5 to 8 times of its original length before lamination. Adjacent stretch rolls may be 10 to 150 mm apart. Basis weight of the laminate is 40 to 100 g/m$^2$ and basis weight of the elastic film is 20 to 60 g/m$^2$.

A US Publication 2004/121683 discloses a composite elastic material comprising a two sided elastic layer. A gatherable layer is bonded to either side of the elastic layer. The elastic layer and the gatherable layer may be further entangled with a fibrous material. The entangling may be performed with high pressure liquid jets.

A PCT Publication WO2008/067463 introduces an elastic laminate fabrication process with cross-direction stretch that supplements machine direction stretch. An elastic film is stretched to 50% of its length along the machine direction before lamination stage. In addition, the elastic film layer is stretched to 20% or more of its original length in cross direction before lamination stage. The elastic laminate recovers 50% stretch.

Upon removal of the stress, the TEM film may retract back due to its elastic properties. Upon retraction of the TEM film, the envelope web(s) bonded to the TEM film may be drawn along with the TEM film. The envelope web(s) may accumulate between bonding sites upon stress removal, thus rendering the elastic laminate with elastic properties in direction of the stretch. However, the TEM film bonded to the envelope webs may not achieve desired amount of retraction even upon removal of stress. Limited retraction of the TEM film may hinder the elasticity and flexibility of the elastic laminate.

The elastic laminate may further be stored to provide a relaxation time for the laminate. The laminate may undergo re-contraction or re-covering during the relaxation time on removal of all kinds of stress during the time. However, none of the prior arts discloses significance of the relaxation time in the elastic laminate manufacturing.

SUMMARY

An elastic laminate may be manufactured by bonding an elastic Thermoplastic Elastomeric Material (TEM) film to at least one envelope web(s). To this end, a carrier web is provided by a carrier web supply. The carrier web may be a non-woven material, such as a spunbonded web material, and may exhibit basis weights of less than 100 g/m$^2$, preferably less than 50 g/m$^2$, even more preferably less than 20 g/m$^2$, though typically more than about 5 g/m$^2$. A polymer supply may select and feed the TEM polymer, e.g. a polyolefin like polyethylene or polypropylene, e.g. in pellet form, and optionally comprising additives, into an extruder. The TEM may be extruded by the extruder through an extrusion die head to form a coating of TEM film layer on the carrier web, thereby forming the first extruded laminate.

The TEM film layer coated on the carrier web may exhibit a basis weight that may be less than about 100 g/m$^2$, preferably less than about 60 g/m$^2$ or even less than about 40 g/m$^2$, though typically more than about 10 g/m$^2$ or even more than about 20 g/m$^2$, and is allowed to solidify on the carrier web to form a first laminate, wherein the carrier restrains essentially all of the extensibility of the extruded film. Optionally, side margins of the laminate may be trimmed straight. The first laminate may be stored in a first storage prior to further processing of the first laminate. The first laminate may be stored in a wound state on a roll or spool or in a boxed state, preferably under low tension conditions. Further, the first laminate may be delivered to an unwinding or unboxing unit.

The unwound or unboxed first laminate is delivered to a delamination unit. The first laminate is delaminated in the delamination unit by separating the TEM film from the carrier web. The separated carrier web may be reused or recycled as the carrier web supply, if no side trim has been removed after the extrusion step. The extracted TEM film from the delamination unit may be delivered to a stretching station. The stretching station comprises of a plurality of web guide means in order to stretch the extracted delaminated TEM film in a Machine Direction (MD). The web guide means comprises a plurality of rolls rotating at a predetermined speed in order to stretch the TEM film in Machine Direction (MD).

The TEM film may be optionally stretched in Cross Direction (CD) before, during or after stretching the TEM film in Machine Direction (MD). The Cross Direction (CD) stretching of the TEM film may be achieved by passing the Machine Directional (MD) stretched TEM film through the web guide means. The web guide means may comprise tentering frames, rounded bars, etc.

Further, a first envelope web supply provides a first envelope web and optionally a second envelope web supply provides a second envelope web. The stretched TEM film, the first envelope web and the second envelope web, if present, are provided to a bonding unit. The stretched TEM film is positioned in a facing relationship to the envelope web(s). The bonding unit connects the stretched TEM film, the first envelope web and optionally the second envelope web together, thereby forming a second bonded laminate. Optionally, the first or second envelop web may exhibit cross-directional extensibility.

The second bonded laminate may be unstretched by an unstretching means prior to being stored in a second storage. The unstretching means comprises of a plurality of rolls to release stretch of the second laminate. The unstretched second laminate may be allowed to relax for a predetermined time by storing the second laminate in the second storage. The second relaxed laminate may be delivered to a winding station at end of relaxation time to form a roll or spool under a controlled tension, thereby forming the elastic laminate.

Thus, the present invention is a method for manufacturing an elastic laminate, and comprises:

selecting and feeding a Thermoplastic Elastomeric Material (TEM) from a polymer supply (104) into an extruder (106);

extruding the TEM by the extruder (106) through an extrusion die head (108) to form a TEM film layer on a carrier web (101) provided by a carrier supply (102);

solidifying the TEM film layer on the carrier web (101) to form a first laminate (113);

storing the first laminate (113) in a first storage (111);

delivering the first laminate (113) from the first storage (111) to a delamination unit (112) and delaminating the first laminate by separating the TEM layer from the carrier web, wherein optionally the separated carrier web is reused by the carrier supply (102);

stretching the delaminated TEM layer (115) in its machine direction in a stretching station (114) via a plurality of web guide means (117);

positioning the stretched TEM layer (115) between a first envelope web supplied by a first envelope web supply (116), and optionally a second envelope web supplied by a second envelope web supply (118), feeding the stretched TEM layer (115), the first envelope web and the second envelope web to a bonding unit (120) and connecting them to form a second bonded laminate;

releasing stretch of the second bonded laminate via an unstretching means (126)

storing the unstretched second laminate in a second storage (122) for at least 6 hours, more preferably more than 12 hours or even more than 24 hrs, but preferably less than 48 hours, and more preferably less than 36 hours; and winding the second laminate under controlled tension, preferably at a winding tension range of from about 15 N (1.5 kgf) to about 100 N (10 kgf) for a web width of between 15 cm and 150 cm to form a roll or spool, corresponding to aa range from about 50 to 200 N/m, thereby forming the elastic laminate.

The carrier web, the first envelope web and the second envelope web preferably comprise a non-woven web, preferably selected from the group consisting of meltblown web, spunbond web, bonded carded web, airlaid web, coform web or hydraulically entangled web.

The storing of the first laminate in the first storage (111) may be in a wound-up or boxed state under low tension conditions, preferably at less than 15 N/m. The bonding step in the bonding unit (120) may be heat fusion bonding, preferably ultrasonic bonding.

The MD stretching of the TEM layer prior to bonding may be stretching the TEM layer by at least 20% and less than 200%. The MD stretching of the TEM layer may result in a neck-down of reducing the width of the TEM layer before being stored in storage 122 to between 60% and 80% of the width prior to the delamination step.

The neck-down after the stretching step is preferably mitigated by the storing step such that the width of the TEM layer after being stored is at least 5%, preferably at least 10% more than the width of the TEM layer before being stored in storage 122.

Preferably, the machine directional speed of the carrier web in the extrusion step may be less than about 100 m/min, and may be lower than the machine directional speed of the stretched TEM layer and the envelope webs in the bonding unit.

Optionally, the method may further comprise the step of cross-directionally stretching the TEM layer prior to feeding it to the bonding unit, which may be performed before, during or after the step of machine-directional stretching.

Optionally, the bonded laminate may be apertured after being laminated, preferably by hot needle punching.

Preferably, the selecting of the TEM is made from a modified metallocene catalyzed polyolefin, more preferably polyethylene and polypropylene.

BRIEF DESCRIPTION OF THE DRAWINGS

Same numerals in different figures refer to same or equivalent features. Figures are schematic and not to scale.

DETAILED DESCRIPTION OF THE DRAWINGS

Figure 1:
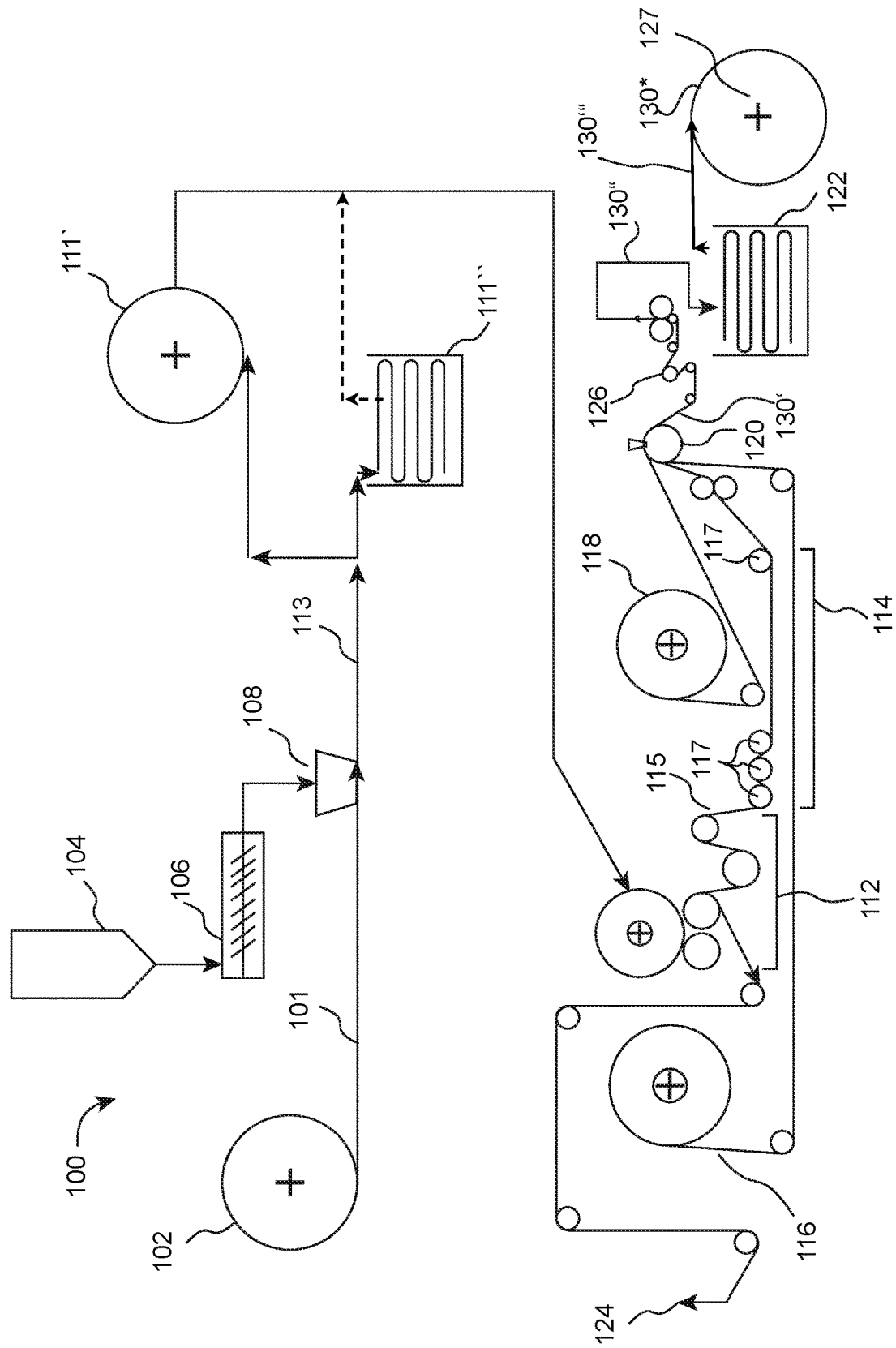
FIG. 1 illustrates an elastic laminate manufacturing process according to the present invention.

Reference now will be made in detail to various embodiments of the invention, one or more examples of which are set forth below. Each example is provided by way of explanation, not limitation of the invention.

An elastic bonded laminate may be manufactured according to the present invention by bonding an elastic Thermoplastic Elastomeric Material (TEM) film to at least one envelope web. The TEM film may be made up of material such as, but not limited to modified metallocene catalyzed polyolefin polymers such as polyethylene or polypropylene. The metallocene based polyolefin compounds exhibit unique properties rendering them highly useful in manufacturing of the TEM film. The TEM polymers made from the metallocene catalyzed polyolefin also exhibit film clarity, high tensile strength and less extractables content. The polymers further comprise improved stiffness, high gas barrier properties, significant flame retardancy, and high crystallization rates.

A carrier supply provides a carrier web. The present invention discloses, but is not limited to, number of carrier webs provided by a number of carrier supplies such as nonwoven webs, preferably spunbonded polypropylene webs. A polymer supply feeds the TEM polymer, e.g. in pellet form and optionally comprising further additives, to an extruder for extrusion. The extruding may be performed at sufficiently high temperature to melt the polymer. The molten polymer may be extruded via an extrusion die head so as to form a TEM film layer or coating on the carrier web.

Upon solidifying the TEM film layer on the carrier web the first extruded laminate is formed. Optionally, the longitudinal side margins of the first laminate may be trimmed straight. The first laminate may be stored in a wound state or boxed state in a storage prior to further processing of the first laminate. Hence, prior to stretching, bonding and final delivery of the elastic bonded laminate, the first extruded laminate may be unwound or unboxed from the stored state and provided to a delamination unit. The delamination unit may separate the carrier web and the elastic TEM film by delaminating the first laminate. A carrier web obtained by delaminating the first laminate may be recycled or reused by the carrier supply. The delaminated TEM film may further be provided to a plurality of web guide means for stretching the TEM film in machine direction by applying a predetermined level of stress.

Further, the stretched TEM film may be positioned in a facing position to a first envelope web supplied by a first envelope web supply and optionally to a second envelope web supplied by a second envelope web supply to sandwich the TEM film there between. The stretched TEM film, the first envelope web and the second envelope web, if present, may be fed to a bonding unit. The bonding unit connects the stretched TEM film and the envelope web(s) to form the bonded laminate. However, the TEM film bonded to the carrier web(s) may not achieve desired high amount of retraction upon removal of stress. The second bonded laminate is allowed to relax for a predetermined period of time prior to feeding the second bonded laminate to a winding station.

Relaxation of the second bonded laminate achieves the desired elasticity and flexibility performance as desired for further processing or in the article to which such an elastic laminate may be inserted. The elastic laminate may undergo re-contraction or re-covering during the relaxation time on removal of mechanical stress during the time. After at least a predetermined amount of relaxation time, the elastic laminate is delivered to a winding station, where the laminate is wound under a controlled and preferably low tension and stored in a second storage and/or further transported to a converting site in a roll, spool or wound state.

FIG. 1 illustrates an elastic bonded laminate manufacturing process 100 in accordance with the present invention. A polymer supply (104) feeds a Thermoplastic Elastomeric Material (TEM) polymer, typically in pellet form, to an extruder (106). The TEM polymer may be extruded by the extruder (106) through an extrusion die head (108) to form a TEM film layer on a carrier web (101) supplied by a carrier supply (102). The carrier web (101) may suitably comprise a non-woven web. The non-woven web may be selected from, but is not limited to, meltblown web, spunbond web, bonded carded web, airlaid web, coform web, hydraulically entangled web and the like. An exemplary execution may be a spunbonded polypropylene web at about 30 g/m³. The TEM film layer is allowed to solidify in order to form a first extruded laminate (113). The first extruded laminate (113) may be stored in a first storage (111) under low or moderate tension conditions prior to further processing, e.g., in a boxed state (111") or in a loosely wound state (111'), wherein the machine directional strain is primarily taken by the nonwoven of the laminate, such that the film is essentially only strained by the radial pressure of the winding.

The first laminate (113) is delivered to a delamination unit (112) by removing the first laminate (113) from the storage (111), e.g. as shown by unwinding the first laminate (113). Hence, prior to stretching, bonding and final delivery of the elastic laminate, the first laminate (113) is removed from the stored state and provided to a delamination unit (112). The delamination unit (112) separates a carrier web (124) and the elastic TEM film (115) by delaminating the first laminate (113). The carrier web (124) obtained by delaminating the first laminate (113) may be recycled or reused by the carrier supply (102), if it is not being trimmed after the extrusion step. The delaminated TEM layer (115) is further provided to a plurality of web guide means (117) for stretching the TEM film in Machine Direction (MD) by applying a predetermined level of stress in a stretching station (114). The delaminated TEM layer (115) may be further stretched in the Cross Direction (CD) before, during or after stretching the layer in the Machine Direction (MD) (not shown in the figure). The web guide means (117) according to one embodiment of the present invention comprises a plurality of rolls. The plurality of rolls is adapted to stretch the delaminated TEM layer (115) in the Machine Direction (MD). The plurality of web guide means (117) according to another embodiment of the present invention comprises of tentering, rounded bars, etc. in order to stretch the delaminated TEM layer in Cross Direction (CD).

In accordance to another embodiment of the present invention, the machine directional speed of the carrier web under the extrusion die head (108) is lower than the machine directional speed of the stretched TEM layer and said envelope webs (116, 118) in the bonding unit (120).

In an embodiment of the present invention, the TEM film (115) extracted from the delamination unit (112) may be provided to a plurality of web guide means (117) for stretching the extracted delaminated TEM film (115) in a Cross Direction (CD) after stretching in Machine Direction (MD). In another embodiment of the present invention, the Cross Direction (CD) stretching of the TEM film (115) may be performed during the Machine Directional (MD) stretching. Thus, the TEM film (115) may be stretched in both Machine direction (MD) and Cross Direction (CD) by the web guide means (117). The TEM film may be stretched in the Machine Direction (MD) or the Cross Direction (CD) prior to feeding the film to a bonding unit (120).

In accordance to still another embodiment of the present invention, the Machine Direction (MD) stretching of the TEM film leads to stretching of the TEM film by at least 20 percent to a stretch factor of 1.2× relative to its original length. Further, the Machine Directional (MD) stretching of the TEM film may lead to stretching of the TEM film to a maximum of 200 percent, or a stretch factor of 3× relative to its original length. In addition, the Machine Directional (MD) stretching of the TEM film leads to neck-down or reducing width of the TEM film before being stored in a second storage (122) from 60 percent to 80 percent of the width prior to the delamination unit (112). The web guide means (117) comprise an arrangement of a plurality of rollers, where each roller rotates at a predefined speed. Speed of each succeeding roller may be more than speed of preceding roller in series of rollers.

Further, the stretched TEM layer is positioned between a first envelope web supplied by a first envelope web supply (116) and optionally a second envelope web supplied by a second envelope web supply (118). The stretched TEM layer, the first envelope web and the second envelope web, if present, are fed to a bonding unit (120). The bonding unit connects the stretched TEM film and the envelope web(s) to form a second bonded laminate (generally denoted 130). In accordance with an embodiment of the present invention, the bonding unit (120) may preferably be, but is not limited to, heat fusion bonding or ultrasonic bonding. A further bonding method may comprise adhesives, e.g. powder bonding that comprises a powdered adhesive. The powdered adhesive may be dispensed throughout the carrier web. The dispensed adhesive may be activated by applying hot air to the carrier web and adhesive.

Further, a bonding method, known as pattern bonding may preferably be used to bond the carrier web and the TEM film. The pattern bonding comprises rolls exhibiting a structured surface that interact with a counter roll. Energy is transferred to the materials in the nip between the pattern and the counter roll, such as by pressurizing or heating of at least one of the rolls or preferably by ultrasonic energy bonding method may be adopted to bond fibers of molten TEM film in a localized bond pattern with bond points through the bonded laminate. The introduced energy provides melting of at least some of the TEM polymer at bond points corresponding to the structured surface of the pattern roll(s). In the case of employing two envelope webs, the laminate may also be bonded by melting the polymer of the envelope webs, which typically exhibits a higher melting point than the TEM polymer, such that the latter is essentially removed from the bond points, when the molten polymer or the envelope webs solidify thereby accomplishing the bonding. The bonding pattern may extend over the full surface of the laminate, optionally exhibiting a uniform pattern.

The second stretched bonded laminate (130') is provided to an unstretching means (126) wherein the stretch is released in the unstretched bonded laminate 130". The TEM film comprising elastic properties retracts back towards, but not completely to its original dimensions upon removal of the stretch. As the TEM film is bonded to the envelope webs comprising non-woven webs, upon removal of stretch, the envelope webs gather in the elastic laminate between bonding sites. The gathering of the envelope webs leads to development of elastic and flexible properties in the elastic laminate (130").

However, the TEM film bonded to the envelope webs may not immediately achieve the amount of retraction as desired for the further processing even upon removal of stretch. Therefore, the unstretched bonded laminate (130") is allowed to relax for a predetermined period of time before this relaxed bonded laminate 130''' is fed to the final winding station (127). The relaxed bonded laminate (130''') attains softness and fine texture during relaxation period. The unstretched bonded laminate (130''') is stored in the second storage (122) to allow relaxation. The laminate is stored for at least 6 hours, more preferably more than 12 hours or even more than 24 hrs, but preferably less than 48 hours, and more preferably less than 36 hours. The minimum required time of the relaxation period significantly effects properties of the elastic laminate. The time of the relaxation period also effects neck-down of width of the elastic laminate.

Upon allowing the elastic laminate to relax in the storage (122) for above mentioned time periods, the relaxation also tends to mitigate neck-down effects born to the Machine Directional (MD) stretching. The TEM film may have a width of at least 105 percent after relaxation time period. The achieved width gain during relaxation may be at least 10 percent more than the width of the TEM film before being stored in the second storage (122). This effect is even more pronounced, if the envelope web(S) exhibit a certain cross-directional extensibility, such as may be achieved by using webs as described in the above referenced U.S. Pat. No. 6,746,978 (WARD)

The relaxed second laminate (130''') is delivered to a winding station (127) after the relaxation period. The laminate is wound under controlled tension at a tension range from about 15 N (1.5 kgf) to about 100 N (10 kgf) for a web width of between 15 cm and 150 cm to form a roll or spool, corresponding to between about 50 and 200 N/m, thereby forming the final bonded elastic laminate (130*).

Figure 2:
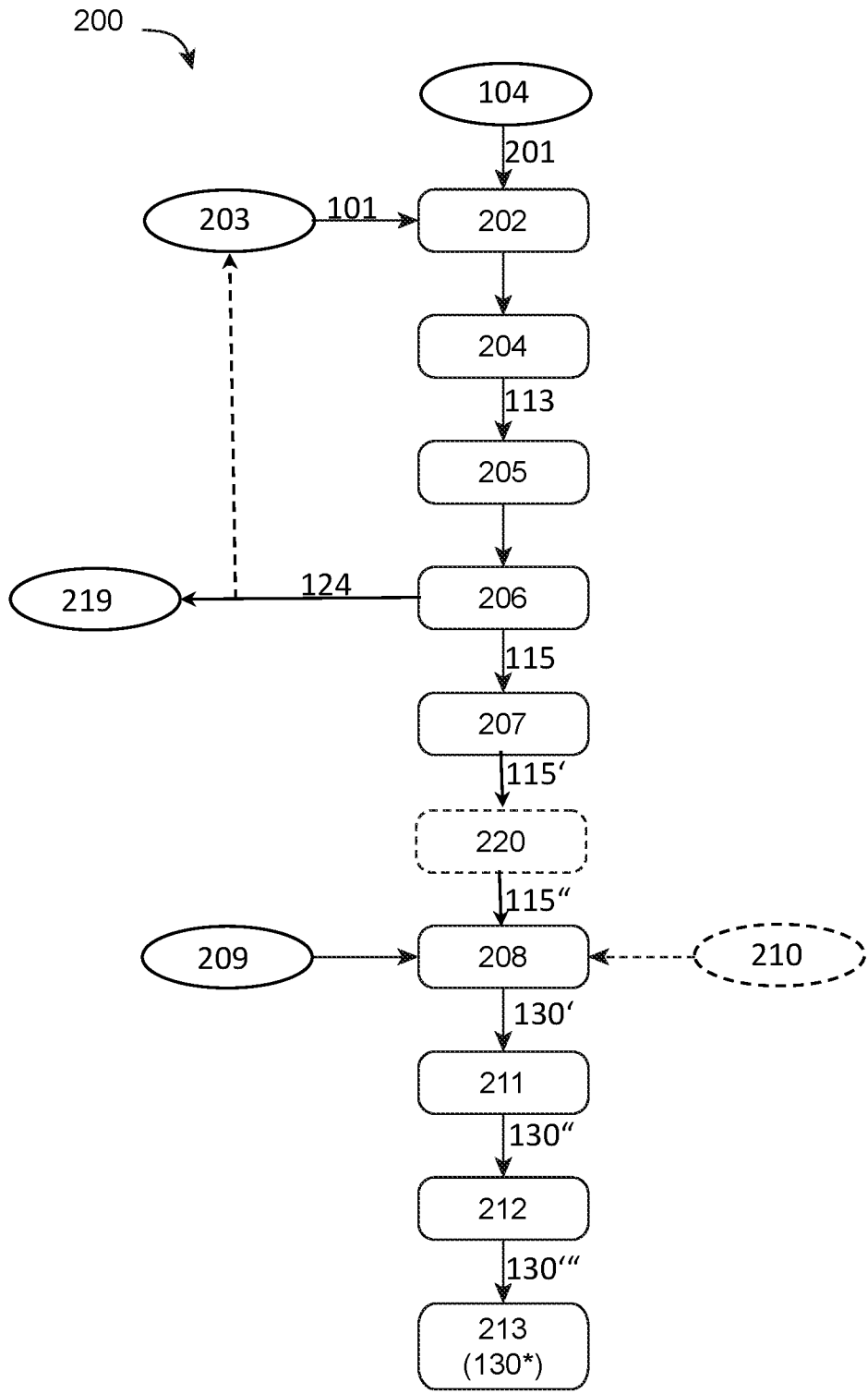
FIG. 2 illustrates a process flow chart for manufacturing an elastic laminate.

FIG. 2 shows a flow chart illustrating a process (200) for manufacturing an elastic laminate in accordance with embodiments of the present invention, such as depicted in FIG. 1. Therein, optional features are depicted with dashes. The process comprises providing a TEM polymer (201) from a polymer supply (104). The TEM polymer may be made up of a material from a group, but is not limited to modified metallocene catalyzed polyolefin such as polyethylene or polypropylene. Further, the TEM polymer is extruded (202) by an extruder (106) through an extrusion die head (108) to form a TEM film layer on a carrier web (101) as provided (203) by a carrier supply (102). The TEM film coated on the carrier web (101) is solidifying (204) to form a first laminate (113). The carrier web (101) may be made up of a material from a group comprising a non-woven web, preferably selected from the group, but is not limited to, meltblown web, spunbond web, bonded carded web, airlaid web, coform web, hydraulically entangled web and the like. After forming the laminate (204) the first laminate (113) formed from coating of the TEM film layer on the carrier web (101) is stored (205), e.g., in a storage means (111). The laminate may be stored in either wound state (111') or boxed state (111") in the storage means (111). Most preferably, the first laminate (113) is stored under low tension conditions.

Further, the first laminate (113) is delaminated (206) in a delamination unit (112) after removing, e.g., by unwinding the first laminate (113) from the storage (111'). At delaminating (206), the delamination unit (112) delaminates the first laminate (113) to separate TEM film layer (115) and a carrier web (124). The extracted carrier web (124) may be recycled in an environmentally compatible manner, or, if not trimmed too much, reused via supplying it (203) to the carrier web supply unit (102).

After delaminating (206) the first extruded laminate (113), the delaminated TEM layer (115) undergoes stretching (207) in a stretching station (114) which stretches the delaminated TEM layer (115) in Machine Direction (MD). The delaminated TEM layer (115) is provided to a plurality of web guide means (117) for forming stretched delaminated TEM layer (115'). The web guide means (117) allow lateral positioning of the TEM layer in a precise manner. The web guide means (117) comprise a plurality of rollers spaced apart at a distance. Each roller may have a predetermined speed, where preferably each succeeding roller may have increased speed than its preceding roller. The web guide means (117) further helps to maintain a uniform tension across the lateral position of the TEM layer. Stretching by the web guide means (117) ensures alignment of the TEM layer with respect to the Machine Direction (MD) center line in manufacturing of the elastic laminate. The web guide means (117) further avoids bending of the TEM layer in Cross Direction (CD).

In accordance to another embodiment of the present invention, the stretching (220) may alternatively or additionally be performed in Cross Direction (CD), e.g., after stretching the delaminated TEM layer in the Machine Direction (MD). The Machine Direction (MD) stretching may refer to stretching of the TEM layer along length in which the TEM film is produced while the Cross Direction (CD) stretching may refer to stretching the TEM layer in a direction perpendicular to the machine direction. Stretching of the TEM layer is performed in the Cross Direction (CD) by passing the delaminated TEM layer through the web guide means (117). The web guide means (117) may comprise tentering, rounded bars, etc., in order to stretch the delaminated TEM layer in Cross Direction (CD) and resulting in a bi-directionally stretched TEM layer 115".

The Machine Direction (MD) stretching (207) of the TEM layer leads to stretching of the TEM layer by at least 20%. In addition, stretching of the TEM layer in Machine Direction (MD) also leads to stretching of the TEM layer by a maximum of 200%. The TEM layer being made up of elastic material may retract or recover back its original dimensions upon removal of stretch. The Machine Direction (MD) stretching of the TEM layer further results in a neck-down of width of the TEM layer. The necking of the TEM layer leads to reducing width of the TEM layer prior to being stored in a storage. The necking of the TEM layer results in reduction of width of the TEM layer between 60% and 80% of the width prior to the delamination step. The TEM layer may be Cross Directional (CD) necked to 70% due to the Machine Direction (MD) stretching prior to bonding.

The stretched TEM layer undergoes bonding (208) in a bonding unit (120). A first envelope web is provided (209) by a first envelope web supply (116), and optionally a second envelope web is provided (210) by a second envelope web supply (118). The first envelope web and the second envelope web, if present, are fed together with the stretched TEM layer (115) to the bonding unit (120) to form a second stretched bonded laminate (130"). The first envelope web and the second envelope web may be made up of a non-woven web material selected from, but is not limited to, meltblown web, spunbond web, bonded carded web, airlaid web, coform web, hydraulically entangled web and the like. When a second envelope web is present, the stretched TEM layer (115) is positioned between the first envelope web and the second envelope web in the bonding unit (120). The bonding unit (120) that bonds the TEM layer, the first envelope web and the second envelope web, if present, may utilize any kind of bonding technique already known in the art. The bonding technique may be applying glue or activating glue as may be present in at least one web, preferably be thermal energy or heat, more preferably ultrasonic bonding. The bonding process bonds the TEM layer to the fibers of the one or more envelope webs made up of non-woven webs.

Preferably, Machine Directional (MD) speed of the carrier web in the extrusion step (202) is lower than the Machine Direction (MD) speed of the stretched TEM layer and the envelope webs in the bonding unit (208).

The second bonded stretched laminate (130') is formed (208) by bonding the TEM layer, the first envelope web and the optional second envelope web in the bonding unit (120). The second bonded stretched laminate (130') undergoes unstretching (211) by delivering it to an unstretching unit (126). The unstretched bonded laminate (130") is further stored (212) under low, preferably no, tension in a storage box (122) for a predetermined amount of time. Storing the unstretched bonded laminate (130") for the predetermined time relaxes the unstretched laminate in order to allow the laminate to recover or retract back to a certain percentage of its original dimensions prior to being delivered to further processing, e.g., a diaper converter. The time of relaxation of the unstretched bonded laminate is at least 6 hours, more preferably more than 12 hours or even more than 24 hrs, but preferably less than 48 hours, and more preferably less than 36 hours. The neck-down of the TEM layer may be mitigated by storing the TEM layer. Typically, the width of the TEM layer after being stored differs less than 10%, preferably at least 5% less from the width of the TEM layer before being stored in the storage.

The relaxation of the unstretched laminate for the predetermined time is an important requirement in manufacturing of the laminate. The unstretched relaxed laminate (130''') may have desired elasticity, softness, tenderness, etc. The unstretched relaxed laminated (130''') is delivered to a winding station to perform winding (213). The laminate is wound in the form of a roll or spool at the winding station under controlled tension. The unstretched relaxed laminate is wounded at a winding tension range from about 15 N (1.5 kgf) to about 100 N (10 kgf) for a web width of between 15 cm and 150 cm to form a roll or spool, corresponding to a range of from 50 to 200 N/m, thereby forming the spooled or rolled final elastic laminate (130*).

Figure 3:
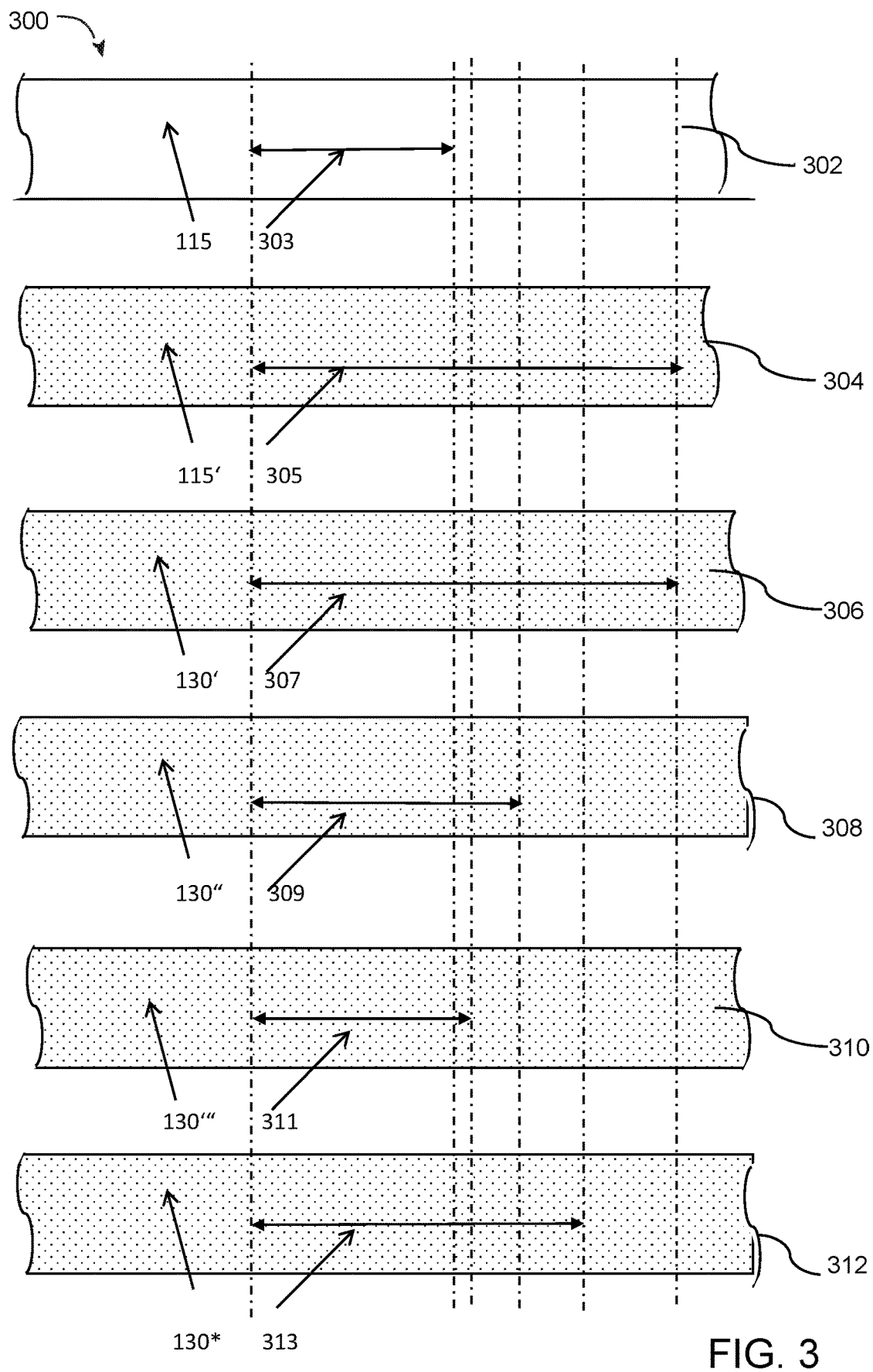
FIG. 3 illustrates various stages depicting the percent stretch of the elastic laminate during the manufacturing process.

FIG. 3 illustrates exemplarily various stages 300 depicting percent stretch of the elastic laminate during various stages of the manufacturing process as described in the above. The percent stretch may refer to ratio of increased dimension of the elastic laminate to original dimension of the elastic laminate.

The delaminated TEM layer (115) is essentially unstretched and exhibits a unit length (303) of 100% in machine direction as shown at stage 302 with reference to FIG. 3. After undergoing the stretching in stretching unit with web guide means (117), the stretched TEM layer (115') exhibits a stretched elongation, e.g. of 100% (i.e. with a stretch factor of 2× or twice as long as the unit length of the unstretched material, see 304). When the stretched TEM layer is bonded to the one or more envelop webs, the stretch (307) remains essentially constant and the bonded stretched laminate (130') is formed (see 306)

Upon releasing the stress, the bonded stretched laminate (130') contracts quickly to the unstretched bonded laminate 130", at an elongation (309) of e.g. 10% of the original unit length or a stretch factor of 1.1× (see 308).

The second bonded unstretched laminate is further allowed to relax by being stored in a storage (122). The relaxation of the laminate in the storage leads to further retraction of the laminate in its length. As shown in FIG. 3, after relaxation, the unstretched relaxed bonded laminate (130''') may exhibit a an elongation (311) of e.g. between 2% (or 1.02×) and 10% (or 1.1×), which is less than the elongation before relaxation, though still slightly larger than of the unstretched TEM layer. After storage of the unstretched relaxed laminate for the predetermined time, the laminate is delivered to a winding station. The laminate may be wound under controlled tension, preferably at a winding tension range of from about 15 N (1.5 kgf) to about 100 N (10 kgf) for a web width of between 15 cm and 150 cm to form a roll or spool, thereby forming the final elastic laminate (130*) which may the exhibit a somewhat increased elongation (313), e.g. of 10% (1.1×) (see 312).

FIGS. 4 A to E illustrate another embodiment of the present invention representing change of width or neck down effect 400 of an elastic laminate due to Machine Direction (MD) stretching in the process according to the present invention, as described in the above. The first extruded laminate (113) is only slightly strained, and the strain is essentially absorbed by the carrier web, such that the TEM layer is essentially unstretched and hence there is practically no neck down. Thus, the extruded TEM layer on the carrier web of the first extruded laminate (113) may have a cross direction unit width (402) of to 100%.

Figure 4A:
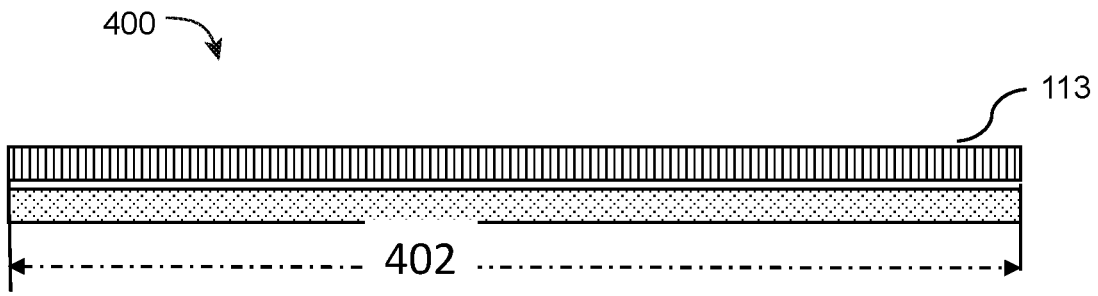
FIGS. 4A to 4E illustrate width or neck down effect in the elastic laminate due to machine direction stretching.
Figure 4B:
Figure 4C:
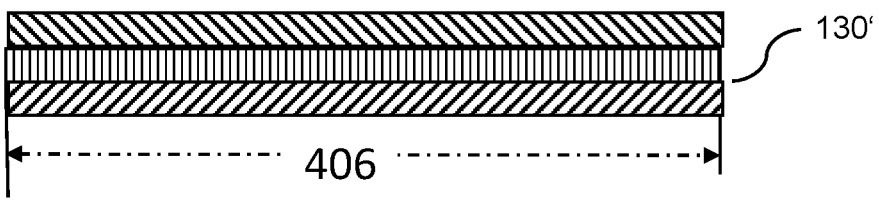
Figure 4D:
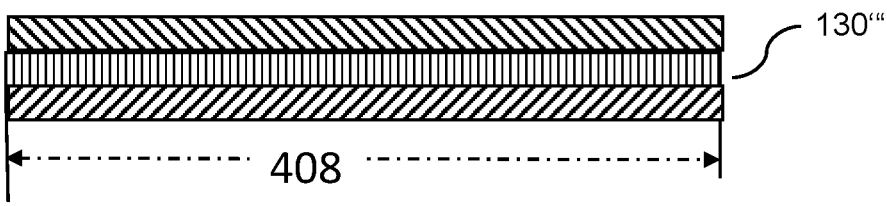
Figure 4E:
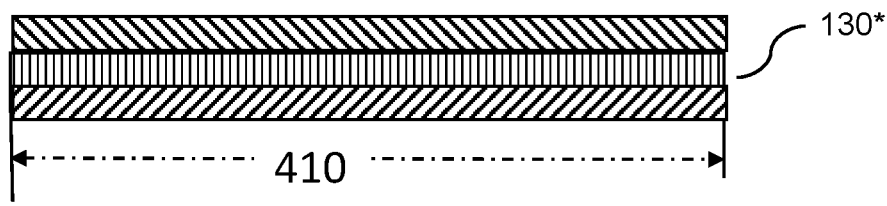

Once delaminated, the TEM layer (115) is provided to a plurality of web guide means (117) forming the delaminated stretched TEM layer (115'). As shown in FIG. 4B, by stretching the delaminated TEM layer in Machine Direction (MD) in the absence of CD stretching, the delaminated stretched TEM layer (115') is reduced in width (404). The width reduction may be referred to as neck down effect. The Machine Direction (MD) stretching of the TEM layer may lead to a Cross Directional (CD) width of e.g. about 80%, 70% or even 60% or less of the original unit width (402).

The stretched TEM layer is delivered to a bonding unit (120) along with envelope web(s) to form a second stretched bonded laminate. The bonding does not result in any neck down or reduction in width (406) of the second bonded stretch laminate (130') in Cross Direction (CD), see FIG. 4C. The second bonded stretched laminate is further delivered to an unstretching means (126). During relaxation, the unstretched laminate does essentially not undergo further cross-directional retraction. The unstretched relaxed laminate (130''') is further provided to a winding station, where it is wound under controlled tension at the winding station. Preferable winding tension range may be from about 15 N (1.5 kgf) to about 100 N (10 kgf) for a web width of between 15 cm and 150 cm to form a roll or spool, thereby forming the final elastic laminate (130*), also exhibiting essentially the same width (410) as the relaxed laminate.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

The invention claimed is:

1. A method for manufacturing an elastic laminate, the method comprising:
   selecting and feeding a Thermoplastic Elastomeric Material (TEM) from a polymer supply into an extruder;
   extruding said TEM by said extruder through an extrusion die head to form a TEM film layer on a carrier web provided by a carrier supply;
   solidifying said TEM film layer on said carrier web (101) to form a first laminate;
   storing said first laminate in a first storage;
   delivering said first laminate from said first storage to a delamination unit and delaminating said first laminate by separating said TEM layer from said carrier web,
   stretching said delaminated TEM layer in its machine direction (MD) in a stretching station via a plurality of tentering, rounded bars;
   positioning said stretched TEM layer adjacent to a first envelope web supplied by a first envelope web supply,
   feeding said stretched TEM layer, said first envelope web and a second envelope web to a bonding unit and bonding them to form a second bonded laminate;
   releasing stretch of said second bonded laminate via a plurality of rolls
   storing said unstretched second laminate in a second storage for at least 6 hours; and
   winding said second laminate under controlled tension to form a roll or spool, thereby forming said elastic laminate.

2. The method according to claim 1, wherein said carrier web, and said first envelope web comprise a non-woven web.

3. The method according to claim 1, wherein said storing of said first laminate in the first storage is in a wound-up or boxed state under low tension conditions.

4. The method according to claim 1, wherein said bonding step in said bonding unit is heat fusion bonding or ultrasonic bonding.

5. The method according to claim 1, wherein said MD stretching of said TEM layer is stretching said TEM layer by at least 20% (1.2X) and less than 200% (3X).

6. The method according to claim 1, wherein said MD stretching of said TEM layer is resulting in a neck-down of reducing the width of said TEM layer before being stored in storage 122 to between 60% and 80% of the width prior to the delamination step.

7. The method according to claim 6, wherein said neck-down is mitigated by said storing step such that the width of said TEM layer after being stored is at least 5% more than the width of the TEM layer before being stored in storage 122.

8. A method according to claim 1, wherein the machine directional speed of said carrier web in said extruding step is lower than a machine directional speed of said stretched TEM layer and said envelope webs in said bonding unit.

9. The method according to claim 1 further comprising the step of cross-directionally stretching said TEM layer prior to feeding it to said bonding unit.

10. The method according to claim 9, wherein said cross-directional stretching is performed before, during or after said step of machine-directional stretching.

11. The method according to claim 1, further comprising the step of aperturing the second laminate.

12. The method according to claim 1, wherein said selecting of said TEM is made from a group consisting of modified metallocene catalyzed polyolefin.

13. The method according to claim 1, wherein optionally said carrier web separated from the TEM layer is reused by said carrier supply.

14. The method according to claim 1, wherein the second envelope web is opposite to said first envelope web and supplied by a second envelope web supply.

15. The method according to claim 1, wherein the winding step is performed at a winding tension range of from about 15 N (1.5 kgf) to about 100 N (10 kgf) for a web width of between 15 cm and 150 cm.

16. The method according to claim 2, wherein the non-woven web is selected from the group consisting of melt-blown web, spunbond web, bonded carded web, airlaid web, coform web and hydraulically entangled web.

17. The method according to claim 11, wherein said aperturing is executed by employing hot needle aperturing.

18. The method according to claim 12, wherein said modified metallocene catalyzed polyolefin is selected from the group consisting of polyethylene and polypropylene.

19. The method according to claim 12, wherein said TEM comprises an antiblocking agent selected from the group consisting of Erucamide, Oleamide, and Silica compounds.

* * * * *